United States Patent [19]

Puumalainen

[11] Patent Number: 4,639,942
[45] Date of Patent: Jan. 27, 1987

[54] PROCEDURE FOR MEASURING THE QUANTITY OF SILICON COATING ON PAPER OR CARDBOARD

[75] Inventor: Pertti Puumalainen, Kuopio, Finland

[73] Assignee: Enso-Gutzeit Oy, Helsinki, Finland

[21] Appl. No.: 840,390

[22] Filed: Mar. 17, 1986

Related U.S. Application Data

[63] Continuation of Ser. No. 624,934, Jun. 27, 1984.

[30] Foreign Application Priority Data

Jun. 28, 1983 [FI] Finland ............................ 832344

[51] Int. Cl.$^4$ .................................. G01N 23/223
[52] U.S. Cl. ............................. 378/045; 378/50; 378/143
[58] Field of Search ............... 378/50, 53, 45, 143, 378/44, 90

[56] References Cited

U.S. PATENT DOCUMENTS

| 2,925,497 | 2/1960 | Bessen | 378/50 |
| 3,102,952 | 9/1963 | Hendee et al. | 378/45 |
| 3,351,755 | 11/1967 | Hasler | 378/45 |
| 3,660,662 | 5/1972 | Puolakka | 378/45 |
| 3,889,113 | 6/1975 | Rhodes | 378/45 |
| 4,147,931 | 4/1979 | Puumalainen | 378/50 |
| 4,377,869 | 3/1983 | Venalainen | 378/50 |

FOREIGN PATENT DOCUMENTS

| 55-94149 | 7/1980 | Japan | 378/53 |
| 958932 | 9/1982 | U.S.S.R. | 378/44 |

Primary Examiner—Craig E. Church
Assistant Examiner—T. N. Grigsby
Attorney, Agent, or Firm—Toren, McGeady & Goldberg

[57] ABSTRACT

The present invention concerns the measuring of a silicon coating on paper or cardboard moving in the form of a continuous web and which may as fillers contain substances containing silicon such as kaolin, or aluminum silicate. By x-ray radiation from a primary radiation source (3) and passing through the web is excited the characteristic x-ray radiation of an element, in a secondary radiation source (7) on the silicon coating side of the paper web (1), having a higher ordinal number than silicon (Si). The exciting radiation is sent obliquely against the surface of the paper or cardboard, whereby the irradiation of the surface is accentuated and the characteristic x-ray radiation of the silicon in the silicon coating can be excited. The exciting radiation also partly excites the silicon in the filler, but in this case it will be accompanied by the characteristic x-ray radiation of the metal associated with the silicate, such as aluminum in the instance of kaolin. These two fluorescence radiations are measured using a semiconductor detector (9) with good energy discriminating capacity, the quantity of silicon coating being calculable from the silicon energy peak recorded in the spectrum from this detector when it is corrected, as in the exemplary case, to eliminate with the aid of the aluminum peak the contribution of the filler and when in the scattered energy peak measured from the spectrum the irradiation correction is taken into account. If there is coating on both sides, two measuring heads are placed one after the other in the web's direction of travel by which the surface fluorescence is recorded from different sides.

7 Claims, 1 Drawing Figure

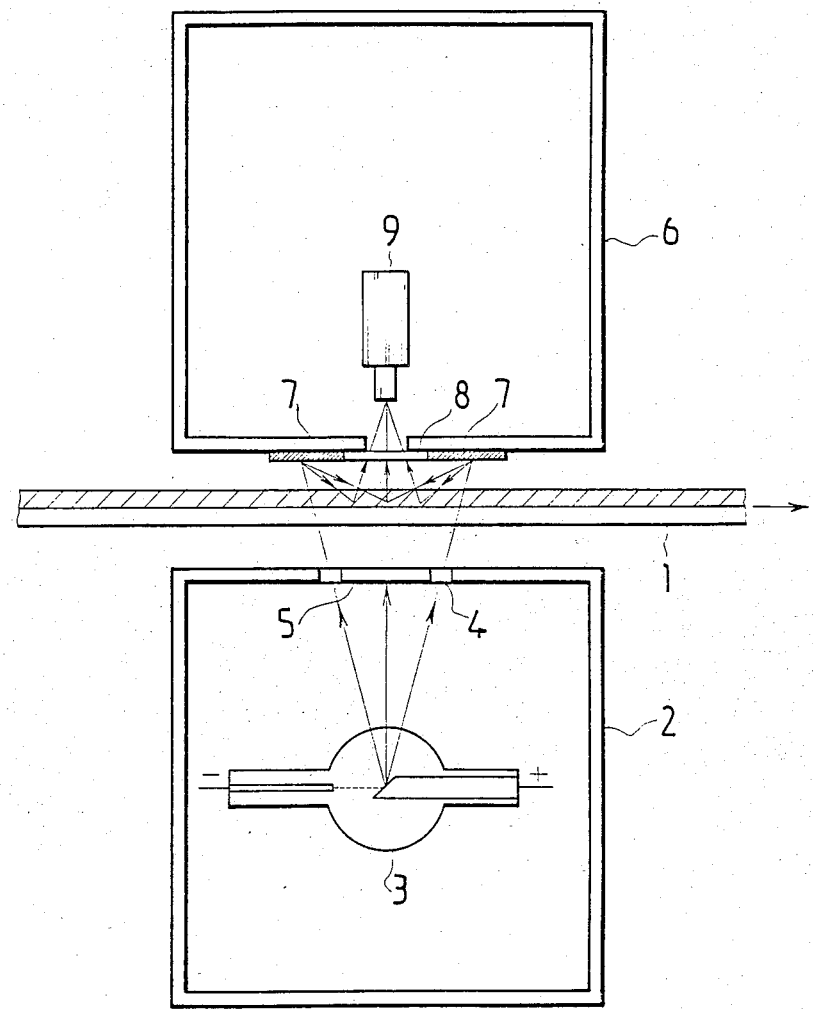

PROCEDURE FOR MEASURING THE QUANTITY OF SILICON COATING ON PAPER OR CARDBOARD

This is a continuation of application Ser. No. 624,934, filed June 27, 1984.

The present invention concerns a procedure for measuring the quantity of silicon coating on paper or cardboard moving in the form of a continuous web on a paper machine or in a paper coating machine. More specifically, the invention concerns the measuring of silicon coating quantity by an on-line method using an x-ray radiation technique, and the intention is to measure silicon coating quantities on various papers, such as grease-proof parchment paper, baking papers and base papers for adhesive paper.

An off-line procedure is known in prior art, in which to the silicon constituting the coating certain tracer elements have been admixed, the fluorescent radiation peaks produced by these enabling the silicon quantity to be determined. However, the intensities of direct fluorescence radiation are low, and in their measurement proportional counters are employed; the most serious drawback of the latter is that they cannot distinguish between the peaks of aluminum (Al) and silicon (Si) in the filler. However, in the paper brands mentioned, fillers are commonly used nowadays, for instance kaolin, one of the aluminum silicates. Therefore, the task of the procedure of the present invention is primarily to be able to determine separately the quantity both of Al and Si so that the effect on the result of measurement from substances containing Al and Si used as fillers in the paper can be eliminated.

Since in view of the price of silicon coating one attempts to keep its quantity as small as possible (an adequate coating of uniform thickness is 0.7–0.8 g/m$^2$), the measuring accuracy should be at least 0.1 g/m$^2$. By the procedure of the invention, which is characterized by that which is stated in the claims following below, it becomes possible to attain the aims mentioned.

In the following an embodiment of the invention is described in detail by a drawing in which FIG. 1 presents in schematic cross-section the apparatus required in carrying out the procedure of the invention.

In FIG. 1, the paper to be measured, travelling as a continuous web, has been indicated with the reference numeral 1, and the silicon coating, in the present instance on its topside, is indicated by cross-hatching. Under the paper web 1 has been disposed a traversing box 2 containing in itself an x-ray tube 3 serving as source of primary radiation, and which may operate e.g. on 10 mA and 10 kV. In order to direct the radiation from the x-ray tube 3 against the paper web 1, a round aperture 4 has been made in the top surface of the box 2, and in the center thereof has been mounted a round radiation shielding plate 5 smaller than the aperture 4; and being very close to the moving paper web 1, this plate also acts as a member damping its fluttering.

The radiation from the x-ray tube 3 is thus only allowed to exit towards the paper web 1 through the gap with the shape of a circular ring left in the aperture 4 by the radiation shielding plate 5.

Opposite to the box 2, above the paper web 1 and in its immediate vicinity, is placed another, identically traversing measuring box 6, on the underside of which has been attached an annular secondary x-ray source 7, positioned accurately in register with the primary x-ray radiation coming from the annular gap of the beam 2. In other words, the secondary source 7 has been placed to be concentric with the aperture 4. The annular secondary source 7 has been made e.g. of elemental sulphur (S). In the center of the ring 7 a round hole 8 has been made in the box 6 for conducting the radiation to a semiconductor detector 9 in vacuum disposed within the box 6. The hole 8 is covered with a window of metallic beryllium admitting a maximal fraction of the incident radiation. It is thus understood that the primary radiation from the x-ray tube 3 has access to the secondary source 7 only from the annular gap in the beam 2 and through the paper web because the radiation shield blocks the path of the rays to the hole 8 and the primary radiation cannot directly strike the detector 9 in the box 6.

The primary radiation supplied by the x-ray tube 3 excites the sulphur atoms of the secondary source 7, which then emit the x-rays characteristic of sulphur, stronger as to their radiant energy than the characteristic x-ray radiations of aluminum and silicon, which are present in the fillers (silicon being present also in the silicon coating on the surface of the paper, of course). This is due to the fact that sulphur (S), selected to be the secondary source 7, comes after aluminium and silicon in the periodic system of elements. For secondary source, also another element may therefore be selected, the most important thing being that the characteristic x-ray radiation emitted by it has higher energy than the excitation energies which the characteristic radiations emitted by the aluminium and silicon in the filler require.

The rays obliquely incident on the paper web 1 from the secondary source 7, and which thus have the longest possible path through the silicon coating, excite the characteristic x-ray radiation of the aluminium and silicon atoms in the coating, as well as partly also the characteristic x-ray radiation of the aluminum and silicon present as filler in the paper web 1 when the filler is kaolin, i.e., aluminium silicate. The characteristic x-ray radiations of all substances—aluminum, silicon and sulphur—pass through the beryllium window in the hole 8 to the detector, from this being obtained a spectrum in which the radiations of different energies produce discrete peaks.

Since the area subtended by the Si peak in the spectrum is proportional to the quantity of the silicon coating with constant irradiation, the quantity of silicon coating can be directly calculated in cases in which the paper contains no kaolin or other filler.

If the paper absorbs in different ways the radiation coming from the x-ray machine, or if the intensity of the x-ray machine varies during the measurement, an irradiation correction is applied by the aid of the scattered S peak; in addition, the filler content and base weight of the paper which affect the scattering pattern of the S peak, determined by another measuring apparatus, may be used in aid. Since now the chemical formula of the filler in the base paper, that is, the proportion of aluminum and silicon therein is known, the contribution to the Si peak from the filler can be eliminated from the Si peak by the aid of the aluminum peak seen in the spectrum, and the part that remains will then be the contribution from the Si in the silicon coating.

The invention is not confined to the embodiment presented above and it may be modified within the claims following below.

I claim:

1. A procedure for on-line measuring of the quantity of silicon coating on paper or cardboard moving as a continuous web and having a first face surface and an oppositely directed second face surface with the silicon coating formed on the first face surface thereof, comprising the steps of producing a primary x-ray radiation with a primary radiation source located on and spaced outwardly from the second face surface of the web, directing the primary radiation through the web from the second face surface to the first face surface and then to a secondary radiation source on the first face surface side of the web and spaced closely outwardly from the web, the secondary radiation source comprising an element having ordinal number higher than that of silicon, and exciting with said primary radiation the characteristic x-ray radiation of said element, directing the characteristic x-ray radiation excited in the secondary radiation source obliquely into the first face surface of the web and thereby exciting the characteristic x-ray radiation of the silicon contained in the silicon coating, collecting the excited characteristic x-ray radiation of silicon in a detector spaced outwardly from the first face surface side of the web, and registering by said detector said excited characteristic x-ray radiation as an indication of the amount of silicon coating, and providing screen means on the first face surface side of the web between the primary radiation source and the web for selectively passing the primary x-ray radiation from the primary radiation source at an oblique angle to the second face surface of the web and then through the web to the secondary radiation source while preventing the primary the x-ray radiation from passing directly through the web to the detector.

2. A procedure according to claim 1, further comprising the steps of providing the secondary radiation source as an annular element which surrounds the projection of the detector toward the web, forming an annular slit by said screen means and passing the primary radiation through the annular slit toward the second face surface side of the web and thereby forming the primary x-ray radiation as a hollow cone for impinging after passage through the web on said annular element, said screen means comprising a circular body defining the radially inner boundary of the annular slit so that the circular body prevents the direct passage of the primary x-ray radiation through the web into the detector.

3. A procedure, as set forth in claim 2, wherein the secondary radiation source has an ordinal number only slightly greater than that of silicon.

4. An apparatus for on-line measuring the quantity of silicon coating on paper or cardboard moving as a continuous web with the web having a first face surface on which the silicon coating is formed and an oppositely directed second face surface, said apparatus comprising a primary x-ray radiation source on the second face surface side of the web and arranged to be spaced outwardly from the web for directing primary x-ray radiation toward the second face surface of the web, a secondary radiation source located on the first face surface side of the web and spaced closely from the web with the secondary radiation source containing an element having an ordinal number higher than that of silicon, a detector located on the first face surface side of the web with the secondary radiation source located between the web and said detector, screen means located on the second face surface side of the web between said primary x-ray radiation source and the web and said screen means arranged to permit the primary x-ray radiation from the primary x-ray radiation source to pass obliquely toward the web while preventing the primary x-ray radiation from passing directly from the primary x-ray radiation source to said detector without contacting said secondary radiation source, such that the primary x-ray radiation passes through the web to the secondary radiation source and then is directed back by said secondary radiation source to the first face surface side of the web for exciting the characteristic x-ray radiation of the silicon within the silicon coating on the first surface side of the web so that the characteristic x-ray radiation is directed to the detector for registering a determination of the amount of the silicon coating.

5. An apparatus according to claim 4, wherein said detector has an axis directed perpendicularly of the web, said secondary radiation source is an annular element encircling the projection of the axis of said detector, said primary x-ray radiation source is positioned in general alignment with the axis of said detector, said screen means comprises an opening in general alignment with said detector and a circular body located within the opening and forming therewith an annular slot so that the primary x-ray radiation passes through said annular slit from said primary x-ray radiation source as a hollow cone with an annular cross section whereby the primary x-ray radiation passes through the web and impinges on said annular element, and said circular body blocks the direct passage of the primary x-ray radiation from said primary x-ray radiation source through the web to the detector.

6. An apparatus according to claim 4, wherein the secondary radiation source is an annular plate formed of an element having an ordinal number only slightly greater than that of silicon.

7. An apparatus according to claim 6, wherein the secondary radiation source is formed of elemental sulphur.

* * * * *